United States Patent [19]

Aldridge et al.

[11] 4,108,310

[45] Aug. 22, 1978

[54] BLOOD PRESSURE TESTING KIT

[75] Inventors: Clarence Foster Aldridge, Asheville; Leo Martin Storey, Jr., Biltmore Forest; Joseph William Cilurzo, Hendersonville, all of N.C.

[73] Assignee: Sybron Corporation, Rochester, N.Y.

[21] Appl. No.: 663,034

[22] Filed: Mar. 2, 1976

[51] Int. Cl.² ............................................. B65D 69/00
[52] U.S. Cl. ................................... 206/570; 206/305; 128/2.05 G; 220/339
[58] Field of Search .............. 206/223, 305, 306, 570; 128/2.05 G; 220/339

[56] References Cited

U.S. PATENT DOCUMENTS

| | | | |
|---|---|---|---|
| 2,624,334 | 1/1953 | Epstein | 128/2.05 G |
| 2,633,237 | 3/1953 | Heyer | 206/223 |
| 2,924,495 | 2/1960 | Haines | 206/305 |
| 3,058,579 | 10/1962 | Morin et al. | 206/223 |
| 3,623,478 | 11/1971 | Saba | 128/2.05 G |

*Primary Examiner*—Stephen P. Garbe
*Assistant Examiner*—Douglas B. Farrow
*Attorney, Agent, or Firm*—Theodore B. Roessel; Joseph C. MacKenzie

[57] ABSTRACT

A blood pressure testing kit having the usual elements, namely, pressure gauge, humeral cuff, pump, bleed valve, and appropriate interconnections, and a stethoscope, is provided with a case which is in two parts hinged together but made of one integral piece of "living hinge" plastic material. One part of the case provides for storing all the said elements but the pressure gauge, which is mounted in the other case part, which acts also as lid for the same part. When the case is open, all the elements are manually accessible for use in blood pressure testing, and at the same time, the pressure gauge can be read while the testing procedure is being carried out.

2 Claims, 3 Drawing Figures

U.S. Patent  Aug. 22, 1978  4,108,310
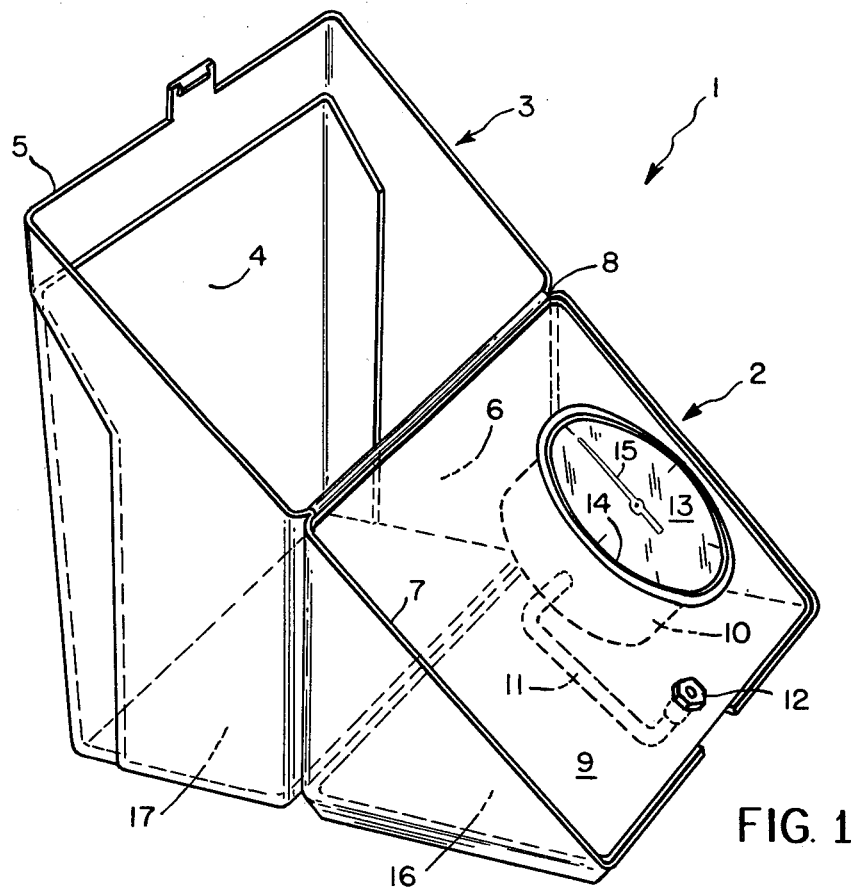
FIG. 1
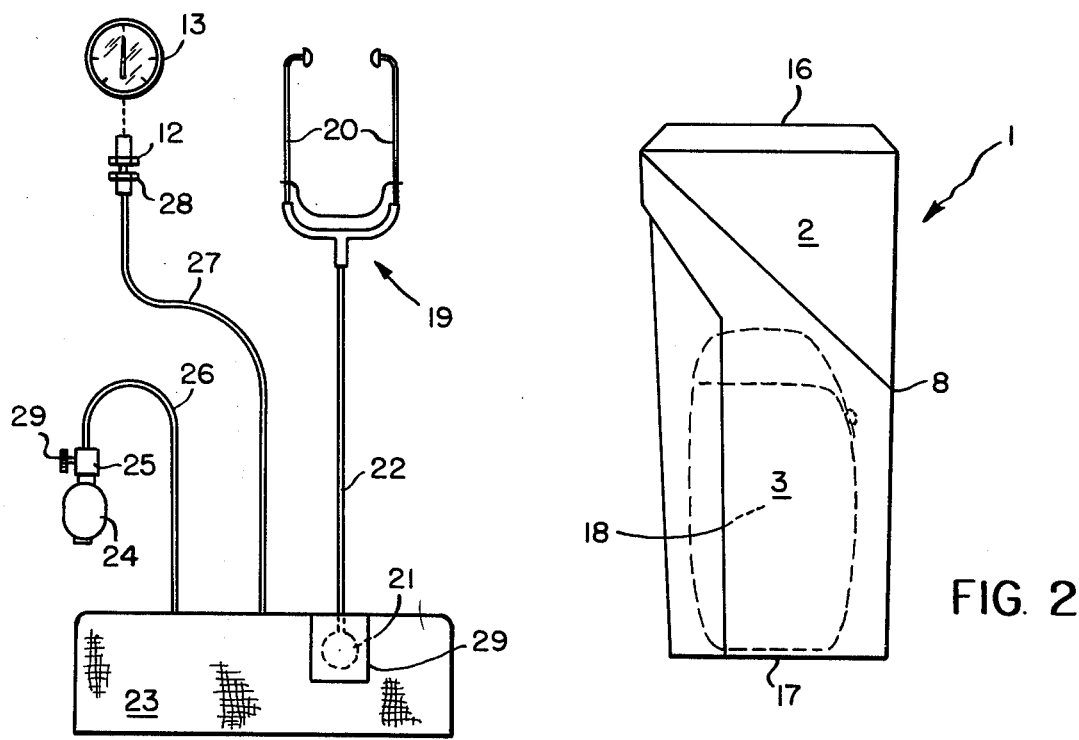
FIG. 2
FIG. 3

BLOOD PRESSURE TESTING KIT

RELATED APPLICATION

U.S. Design Patent Application Ser. No. 608,087, filed Aug. 27, 1975, in the name of John Cuccio, and assigned to the assignee of the present invention.

FIELD OF THE INVENTION

The present invention relates to blood pressure testing wherein an inflatable cuff is wrapped about the upper arm, inflated to the point of totally occluding arterial blood flow, and then allowed to deflate while appearance and disappearance of Korotkow sounds are sensed, and the cuff pressure is observed, in order to determine systolic and diastolic pressure values.

DESCRIPTION OF THE PRIOR ART

The prior art general problem of interest here is that of enabling one to test one's blood pressure, at a time and place of one's own choice. This is of medical value because there are limits on how frequently patients visit their doctors for blood pressure tests. Yet, it is now accepted by many doctors that the blood pressure of patients, who may or do suffer from conditions like hypertension, ought to be monitored frequently, daily, for example.

One resolution of the prior art problem, in our view, and also the general object of our invention, is to provide a blood pressure testing system, particularly adapted for facile and practical home use, by the person whose blood pressure is to be tested, but giving substantially the same results as gotten by that person's doctor or nurse using the usual office-type blood pressure testing system.

SUMMARY OF THE INVENTION

According to out invention, we provide pretty much the usual sphygmomanometric blood pressure testing elements, namely, pressure gauge, cuff, bulb, valve, and appropriaate interconnections, and a stethoscope, in the form of a sort of kit also including a case having one compartment storing all the elements, except the pressure gauge, and a second compartment in which the pressure gauge is mounted and arranged to be easily readable when the case is open and the blood pressure testing elements are in use by one taking one's own blood pressure.

BRIEF DESCRIPTION OF THE DRAWING

FIGS. 1 and 2 are respectively external perspective and elevation views of a blood pressure kit according to our invention.

FIG. 3 is a more or less schematic view of the blood pressure testing elements included in a blood pressure testing kit according to our invention.

DESCRIPTION OF THE PREFERRED EMBODIMENTS

In FIG. 1, reference numeral 1 denotes an open case having compartments 2 and 3. The case is essentially a shell 5 having an open topside 5 and a lid 6 having an open side 7, said lid and shell being connected by a hinge 8. Preferably the shell and lid are molded from polypropylene in one single piece with the two parts being connected by a so-called "living hinge" formed from the polypropylene for providing hinge 8.

The open side of lid 6 is closed by a flat plate 9 which supports a pressure gauge 10, pipe 11, and plug-in pressure coupling element 12. Gauge 10 has a more or less planar reading area 13 including a scale 14 and pointer 15, reading area 13 being substantially coplanar with the margins of open sides 5 and 7, and the plane of plate 9, such plane running diagonally of the plane of the respective top and bottom surface 16 and 17 of the case 1, when the lid 6 and shell 4 are in the open position shown in FIG. 1. The angle between the two planes is chosen to make the reading area 13 readily visible to a person seated at a table, the top of which coincides with surfaces 16 and 17, with shell 4 within easy reach of such person. Conveniently, the case 1, as shown in FIG. 2, may be substantially parallelepipedal, but provided with such tapers, beads, etc., as may be dictated or suggested for aesthetic and manufacturing reasons.

The somewhat amorphous broken-line outline shown with the case interior in FIG. 2 is intended to depict a pouch 18 (omitted from FIG. 1) holding all the elements of FIG. 3 (except gauge 13 and coupling element 12), to wit, stethoscope 19 having binaurals 20 and chest piece 21, interconnected by flexible tubing 22; cuff 23 for wrapping around the upper arm and being secured in position thereon by suitable means (not shown); bulb 24 connected to the interior of the cuff through a bleed valve 25 and flexible tubing 26; flexible tubing 27 connecting at end to the interior of the cuff and having a plug-in coupling element 28 at its other end for plugging into coupling element 12. Bulb 24 is the usual pump for forcing air into the interior of the cuff 23 and valve 29 is the usual bleed device having a knob 29 for adjusting bleed through the valve, to the atmosphere, of air in the cuff. Conveniently, the cuff 23 will have a pocket 29 therein receiving chest piece 21 in such position that when the cuff is correctly placed on the arm and pumped up, the chest piece will be located over the occluded artery where it will later pick-up the Korotkoff sounds while the pressure in the cuff is being bled off.

The arrangement of the elements of FIG. 3 with the case of FIGS. 1 and 2 work a quite substantial improvement in lay blood pressure testing. The conventional system corresponding to FIG. 3, as such, is rather unhandy to use, even for professional people trained in its use, whereas providing the case 1 puts blood pressure testing well within lay person's capacities even when they perform the test on themselves. Besides this, the case performs the conventional function of protecting and compactly harboring all the elements of the sphygmomanometric system which, as FIG. 3 shows, is somewhat unhandy and disorderly in its natural state. Plate 9 provides for mounting a gauge of generously-sized reading area, while still leaving room for operating instructions (not shown), printed or otherwise marked thereon, and blood pressure charts and the like (not shown) can readily be fitted in the compartment 3 along with pouch 18 and its contents.

Having described our invention in accordance with the statutory requirements, we claim:

1. A blood pressure testing kit comprising, in combination, a case and blood pressure testing apparatus,
   (a) said case having a first commmpartment and a second embodiment;
   (b) said blood pressure testing apparatus including a cuff element, a valve element, a bulb element, and pressure coupling and tubing elements;

(c) said blood pressure testing apparatus also including a stethoscope and a pressure gauge couplable by said pressure coupling and tubing elements to other said elements;

(d) said stethoscope and said cuff element being receivable in said first compartment for storage therein, and said pressure gauge being mounted in said second compartment for observation;

(e) said case comprising a hollow shell having an open side for providing said first compartment, a lid having an open side for providing said second compartment and for covering the first said open side, and a hinge securing said lid to said shell;

(f) said hinge providing for swinging said lid about said hinge from a closed position wherein one of said compartments substantially closes the other, to an open position exposing the contents of said compartments to simultaneous external manual and visible access from the same point of view in the external environment and for holding said lid in either said position;

(g) said shell having a flat bottom, said lid having a flat top, and in open position said flat bottom and said flat top being substantially coplanar;

(h) said second compartment having a flat plate closing it, the plane of said plate running diagonally of said lid and having the axis of said hinge therein, and said pressure gauge having a substantially planar reading area coplanar with said plate.

2. The blood pressure testing kit of claim 1 wherein said stethoscope has a chest piece and said cuff element has a pocket for receiving said chest piece.

* * * * *